United States Patent
Murray

(10) Patent No.: US 8,986,014 B2
(45) Date of Patent: Mar. 24, 2015

(54) EVIDENCE-BASED, NEURO-CONGNITIVE TESTING METHODOLOGY, PROTOCOLS AND SYSTEMS

(76) Inventor: Brian Murray, Kingwood, TX (US)

( * ) Notice: Subject to any disclaimer, the term of this patent is extended or adjusted under 35 U.S.C. 154(b) by 49 days.

(21) Appl. No.: 13/506,447

(22) Filed: Apr. 19, 2012

(65) Prior Publication Data

US 2013/0281794 A1   Oct. 24, 2013

(51) Int. Cl.
G09B 19/00 (2006.01)
A61B 5/00 (2006.01)
A61B 5/16 (2006.01)

(52) U.S. Cl.
CPC ... *A61B 5/00* (2013.01); *A61B 5/16* (2013.01); *A61B 5/4088* (2013.01)
USPC ......................................................... 434/236

(58) Field of Classification Search
USPC ................................. 434/236, 238
See application file for complete search history.

(56) References Cited

U.S. PATENT DOCUMENTS

| | | |
|---|---|---|
| 5,200,324 A | 4/1993 | Navaratnam et al. |
| 5,956,125 A | 9/1999 | Rosse et al. |
| 6,306,086 B1 | 10/2001 | Buschke |
| 6,648,834 B2 | 11/2003 | Kajimoto et al. |
| 6,689,058 B2 | 2/2004 | Buschke |
| 6,741,888 B2 | 5/2004 | Musha et al. |
| 6,875,181 B2 | 4/2005 | Kajimoto et al. |
| 7,070,563 B2 | 7/2006 | Buschke |
| 7,314,444 B2 | 1/2008 | Buschke |
| 2003/0180698 A1 | 9/2003 | Salerian |
| 2004/0072261 A1 | 4/2004 | Kostanjevecki et al. |
| 2004/0241757 A1 | 12/2004 | Matsumoto et al. |
| 2005/0196735 A1 | 9/2005 | Buschke |
| 2006/0160146 A1 | 7/2006 | Shimabuku et al. |
| 2008/0124689 A1 * | 5/2008 | Williams et al. ............. 434/236 |
| 2009/0088367 A1 | 4/2009 | Lipton et al. |
| 2009/0285749 A1 | 11/2009 | Idoine et al. |

* cited by examiner

*Primary Examiner* — Kesha Frisby

(57) ABSTRACT

The present disclosure relates to evidenced-based neuro-cognitive testing methodologies and systems. The present disclosure provides for a protocol and testing service. The protocol and testing service provides empirical data support for the interventions of the treating physician or clinician. The evidenced-based neuro-cognitive testing methodology and system disclosed comprises a protocol for the use of a triggering questionnaire. Further, the evidenced-based neuro-cognitive testing methodology and system provides normed screenings to guide and support the interventions provided by the treating physicians or clinicians. The protocol provides for intervention support, interpretations, and empirical data that enhance best practices.

5 Claims, 7 Drawing Sheets

---

Computer instructions for instructing a processor to receive recommendations for a patient from a physician Computer instructions for instructing a processor to perform an algorithm using the interpretation and the physician recommendations to determine an intervention commensurate with the interpretation and the physician recommendations.

EVIDENCE-BASED, NEURO-CONGNITIVE TESTING METHODOLOGY, PROTOCOLS AND SYSTEMS

TECHNICAL FIELD

The present application generally relates to the field of medical testing and provides for a protocol and testing methodology, system and service. More particularly, the present disclosure relates to an evidence-based, neuro-cognitive testing methodology and system. Further, the present disclosure relates to the field of medical and health-rating scales provided within a framework that can be applied to a variety of clinical purposes and settings.

BACKGROUND

The aging of most industrialized country's populations creates a huge need for a system and methodology to identify and treat illness, and to monitor the efficacy of treatment. Further, the aging of most industrialized country's populations creates a need for a system and methodology to identify an illness at an early stage, as reliably as possible.

There exists a long felt need to provide proactive intervention of early stage illnesses. The ability to determine an illness at the earliest possible stage is critical to improving the speed and cost to cure the illness, and after a critical point, no cure may be possible.

A physician's limited time, in most cases, does not allow for the physician to personally implement even a portion of the services required, albeit unknown, by the patient. Further, a physician cannot diagnose maladies or illnesses that should be uncovered, but cannot be, due to time and monetary constraints.

An initial study of the patient to physician ratio in a test geographical target market revealed an approximate average of 5,000 patients per healthcare provider. Existing American Medical Association (AMA) and American Psychological Association (APA) data consistently provides support that approximately 49% of a given population has a diagnosable mental health issue, and a majority of that number may be compounded with co-morbidity. Thus, a large portion of the general population is in a group that requires diagnosis and treatment, but receives no such treatment.

Such data leads to a conservative projection of thousands of unknown patient-consumers in any geographic area that unknowingly need a methodology of diagnosis and treatment. By way of example, and without limitation, available market segments are 7-99 years of age, male or female, households having any range of incomes, educational levels, and occupations, any area serviced by a physician or clinician, all lifestyles, all business organizations, and any religion. None of the identified market areas have any known barrier to the application of this much-needed service.

SUMMARY

The present disclosure provides for a methodology for evaluating specific characteristics of a patient. The patient can visit his or her primary care physician (PCP), who evaluates the patient with respect to the illness presently experienced by the patient. During the office visit with the primary care physician, the patient can complete a questionnaire or similar assessment tool (e.g., the "Murray Neurobehavioral Questionnaire"). The Murray Neurobehavioral Questionnaire provides a basis upon which the need for additional testing (e.g., additional inventories, scales, indices, and/or checklists) can be determined, and responses to the questionnaire are, themselves, also usable to form one or more prospective diagnoses.

The Murray Neurobehavioral Questionnaire is evaluated by the Primary Care Physician, a technician, a computer algorithm, or other similar means, such that direct consultation with a specialist (which can often require weeks or months to schedule) to obtain a report containing prospective diagnoses (which may not be generated for days or weeks following a consultation) is not necessary. If the evaluation of the Murray Neurobehavioral Questionnaire is negative, then no intervention is required. However, if the evaluation of the Murray questionnaire is positive, then the physician can recommend additional assessments, prospective diagnoses, and/or courses of intervention. Rather than consuming a physician's limited time and resources, a technician can explain the process to the patient and input demographic data into the system. The patient thereby completes a computerized assessment that provides meaningful medical information in minutes that would normally require multiple hours of physician interaction.

Standard, normalized data can be used for determining the outcome of the computerized assessment, which can be interpreted by a physician. Based upon the interpretation of the outcome, the physician can make recommendations.

The outcome and associated recommendations can be forwarded to the primary care physician for review between the primary care physician and the patient. The patient, in conjunction with the primary care physician, can determine whether an intervention is required. If the determination is that no intervention is required, the process can be terminated. However, if it is determined that an intervention is appropriate, further action can be taken.

The primary care physician can prescribe an intervention commensurate with the outcome, the recommendations, and the judgment of the primary care physician.

Interventions can include any actions appropriate for the analysis that is based upon the computerized assessment. Such interventions are among those known to persons skilled in the relevant art, and can include, for example, interventions for preventing, addressing, minimizing, and/or eliminating illnesses and maladies, such as depression, a sleep disorder or somnipathy, anxiety, or combinations thereof.

After any patient interventions are conducted, the examining or primary care physician can re-evaluate the patient at set intervals. If the intervention(s) is (are) successful, then the process can be terminated. However, if one or more factors indicate that continuing the interventions would be beneficial, the protocol can continue.

Upon continuation of the process, the patient can complete another computerized assessment, which can be re-evaluated using a similar process as the initial assessment, e.g., the computerized assessment is evaluated using standard, normalized data; a physician interprets the data and makes recommendations to a primary physician; the primary physician reviews the outcome and recommendations and then, subsequently, discusses and reviews the outcome and recommendations with the patient. In doing so, the efficacy of the intervention can be determined. Once again, if it is determined that an alternative and/or additional intervention is required, then additional procedures can be undertaken. If the primary care physician, upon consultation with the patient, determines that no intervention is required, then the protocol can be terminated. The primary care physician can prescribe additional interventions, commensurate with the outcome, the recommendations and the judgment of the primary care physician, to be undertaken by the patient.

From time to time, the patient can visit the examining physician for re-evaluation. During the re-evaluation with the examining primary care physician, the patient can complete additional computerized assessments. This procedure or protocol can continue until such time as the patient has been successfully treated through the interventions by his or her primary care physician and/or other physician(s), as needed.

In another embodiment of the present disclosure, a patient's emotional, social, and occupational functioning can be used in the protocol and/or incorporated into the inquiries with the Murray Neurobehavioral Questionnaire. The patient can select from a battery of choices characteristic of emotional, social, and occupational functioning for providing additional information that may be used in the protocol. For example, a plurality of categories from a General Assessment of Functioning (GAF) scale can be presented to a patient alongside written descriptions of each category, to enable the patient to perform a self-assessment of functionality. A physician can also perform an independent assessment of the patient's functionality, and the patient's response, the physician's assessment, and any differential between the two is usable to determine possible diagnoses and interventions. Response data is exclusive of impairments caused by physical limitations. Thus, response data with respect to a patient's emotional, social, and occupational functioning can be used in the protocol to better define the potential maladies or illnesses to be uncovered.

While certain exemplary embodiments have been described in details and shown in the accompanying drawings, it is to be understood that such embodiments are merely illustrative of and not devised without departing from the basic scope thereof, which is determined by the claims that follow.

BRIEF DESCRIPTION OF THE DRAWINGS

The accompanying drawings, which are incorporated in and constitute a part of this specification, illustrate an implementation of methodology and systems consistent with the present disclosure and, together with the detailed description, serve to explain advantages and principles consistent with the disclosure. In the drawings.

Figure 1:
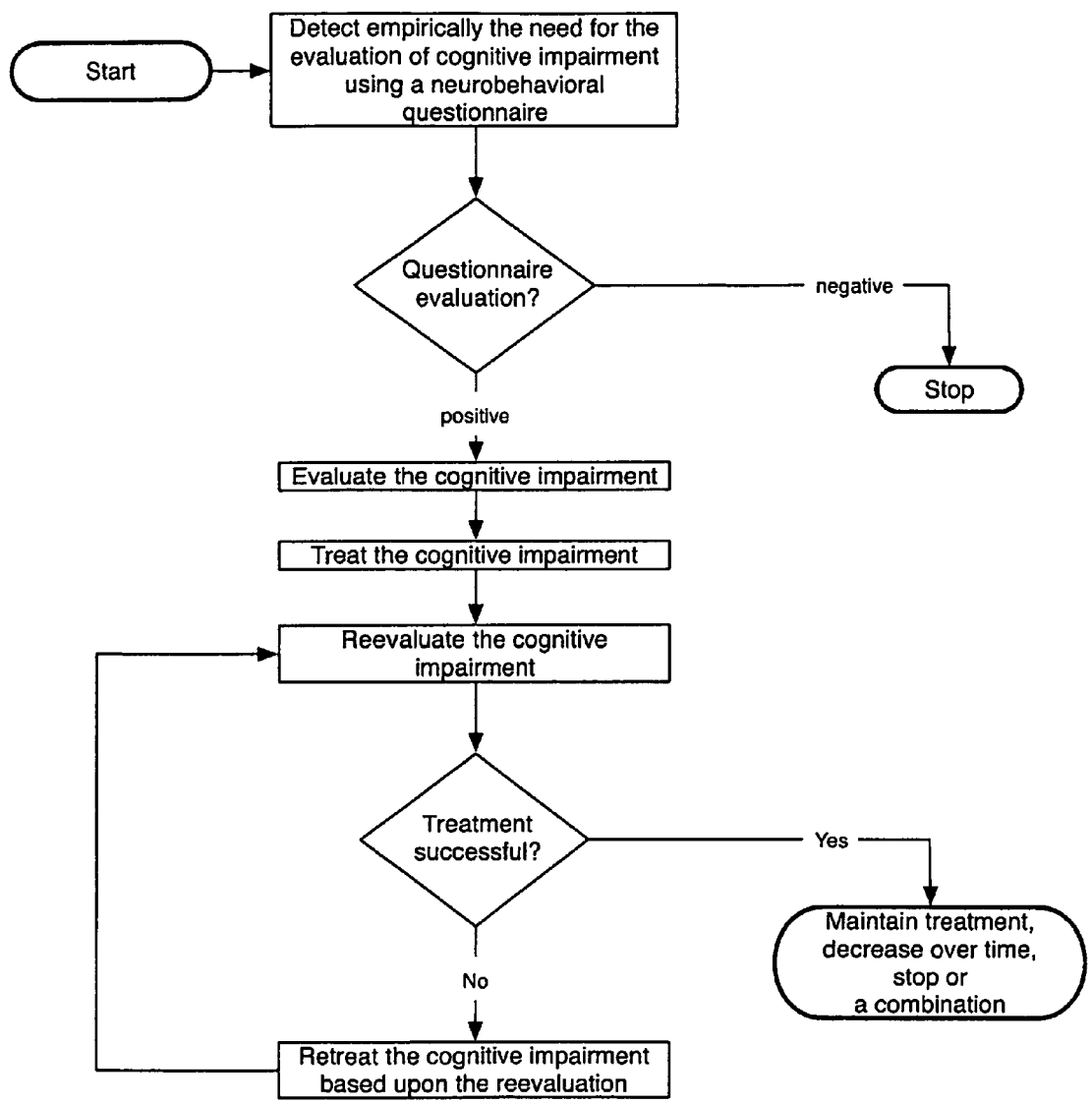
FIG. 1 illustrates a flow chart of an embodiment of an evidence-based, neuro-cognitive testing methodology, protocol and system according to the present disclosure.

The above general description and the following detailed description are merely illustrative of the generic invention, and additional modes, advantages, and particulars of this invention will be readily suggested to those skilled in the art without departing from the spirit and scope of the invention.

DESCRIPTION OF EMBODIMENTS

Before describing selected embodiments of the present disclosure in detail, it is to be understood that the present invention is not limited to the particular embodiments described herein. The disclosure and description herein is illustrative and explanatory of one or more presently preferred embodiments and variations thereof, and it will be appreciated by those skilled in the art that various changes in the design, organization, order of operation, means of operation, systems, methodology, and use of equivalents may be made without departing from the spirit of the invention.

As well, it should be understood that the drawings are intended to illustrate and plainly disclose presently preferred embodiments to one of skill in the art, but are not intended to be manufacturing level drawings or renditions of final products and may include simplified conceptual views as desired for easier and quicker understanding or explanation. As well, the relative size and arrangement of the components may differ from that shown and still operate within the spirit of the invention.

Because many varying and different embodiments may be made within the scope of the concepts herein taught, and because many modifications may be made in the embodiments described herein, it is to be understood that the details herein are to be interpreted as illustrative and non-limiting.

The present application generally relates to methodologies and systems for providing neuro-cognitive testing that is evidence-based. The medical and health rating scales, indices, checklists, inventories, and other similar tools provided within this framework can be applied to a variety of clinical purposes and settings.

For example, medical and health rating scales (e.g., diagnostic tools) provided by the present disclosure can include, without limitation: Quality of Life Tools, AD/HD Tools, Brain Injury Tools, Memory (MCI-Dementia) Tools, Pain Tools, Cancer Tools, Psychiatric Tools (Adults & Pediatrics), Sleep Tools, and Substance Abuse Tools.

The present disclosure provides for proactive intervention. A protocol can be created using triggering techniques and normed screenings. The triggering techniques and normed screenings guide the interventions provided by treating physicians/clinicians. Further, the triggering techniques and normed screenings support the actions and procedures adopted and used by the treating physicians/clinicians. The protocol, methodology and system provide for intervention support, interpretations, and empirical data that enhance best practices.

The primary market for placement of services provided by the present disclosure is, by way of example and without limitation, offices/clinics of Primary Care Physicians, Pain Management Doctors, Orthopedists, Neurologists, Urologists, Internal Medicine practitioners, and Endocrinologists. Further, there exists a need for this service in "boutique medicine" as well as weight management and other practice areas.

Within these practices, as examples, without limitation, the target market of the patient can include: (1) Geriatric, (2) Stroke/TBI/MCI-Dementia, (3) AD/HD, (4) Overweight, (5) suspected or known substance abuse, (6) Diabetics, (7) mood disorders, and (8) behavioral issues.

The present methodology can be implemented as a business-to-business methodology in that its primary market can include physician and/or clinician offices. Alternatively or additionally, the present methodology can include a business-to-consumer methodology that renders protocols and services to the consumer or patient. Additionally, these services are well suited for a business-to-government model, usable to test government employees, school children, and/or a variety of other governmental and/or licensed professionals, such as law enforcement, nursing students, and other similar government or licensed professionals.

No other known methodology includes such protocols, systems, and corresponding infrastructure to provide the unique results and services described herein, in all components, to the physician or clinician base, or to the patient base.

Unique aspects of the present disclosure can include the proprietary triggering aspect of the described systems and methodologies, referred to herein as the "Murray Neurobehavioral Questionnaire," the succinct flow of the protocol, and the unique analysis and/or results achieved by the protocol flow.

As described previously, due to time constraints, a physician often cannot personally implement even a portion of the services provided, pursuant to the disclosed methodology. Accordingly to address the time constraints of the physicians and as a benefit to the physician and the patient, the embodiments, usable within the scope of the present disclosure, unexpectedly and importantly enable a wide range of testing and services to be accurately provided and implemented without requiring the direct administration and/or personal implementation by a physician for the entire protocol.

The quality of the testing can be assured through use of normed tests, which are well established and approved in the medical field for accuracy and correctness, as well as for reimbursement. The speed of delivery of these tests, their interpretations, and accompanying reports are unparalleled. For example, the speed of delivery of these reports may be essentially instant in many cases, and in an embodiment, can be provided within zero to five days or more, depending on any additional analysis and/or interpretation required. In a further embodiment, such reports can be provided within 72 hours. The prices or reimbursement rates are established by the CMS (Centers for Medicare and Medicaid Services). Accepting the third party payer rates for the normed tests is an effective implementation of the present disclosure.

The patent's convenience is thereby greatly enhanced because these services are delivered in the primary care physician's office, where the patient would normally go for traditional services. The methodology and protocol of the present disclosure can be described as ancillary services to what the primary care physician typically provides. As ancillary services, the methodology of the present disclosure can provide a great convenience to the physician by being provided within their office and through his or her practice. Also, as is readily appreciated by those skilled in the art, the fiduciary relationship between the physician or clinician and the use of the present methodology or protocol(s) provides synergistic effects.

The disclosure relates to evidenced-based neuro-cognitive testing methodologies, protocols and systems. The present disclosure provides for protocol, methodology and testing services. The protocol and testing services provide empirical data support for the interventions of the treating physician or clinician. Specifically, the disclosed evidenced-based neuro-cognitive testing methodologies comprise a protocol(s) for the use of a triggering neurobehavioral questionnaire. Further, the evidenced-based neuro-cognitive testing methodology provides normed screenings to guide and support the interventions provided by the treating physicians or clinicians. The protocol(s) provides for intervention support, interpretations, and empirical data that enhance best practices.

A unique aspect of the present methodology is the proprietary neurobehavioral triggering questionnaire and the succinct flow of the protocol. A physician can normally lack sufficient time for the personal implementation of even a portion of the present services, and cost constraints similarly preclude such implementation. The skills necessary to implement the embodiments of the present protocol can be contained within the variety of training obtained by use of the methodology.

FIG. 1 illustrates a flow chart of an embodiment of an evidence-based, neuro-cognitive testing methodology, protocol and system according to the present disclosure.

As shown in FIG. 1, an evidence-based, neuro-cognitive protocol is provided. Empirically the need is detected for the evaluation of cognitive impairment with regard to a patient's condition (e.g., a patient may exhibit signs of dementia or stroke or have a family history of mental health issues, metabolic disorders, or other chronic diseases associated with the development of cognitive impairment, prompting performance of an assessment). If a need for the evaluation of the patient relating to a potential diagnosis of cognitive impairment is not detected, the protocol can be terminated. If a need for the evaluation of the patient relating to a potential diagnosis of cognitive impairment is detected, the cognitive impairment can be evaluated in the patient, e.g., through administration and evaluation of a questionnaire.

The cognitive impairment, including for example, loss of concentration and higher reasoning, learning disabilities, forgetfulness, and other reductions in mental functions, can be treated based upon the evaluation. For example, an intervention can be administered for the underlying cause of a particular reduction in a mental function based on the evaluation, and in some cases, the cognitive impairment can be reversible, if the intervention (e.g., treatment of the patient) is successful.

The cognitive impairment can be re-evaluated for determining the success of the intervention. If re-evaluation determines that the intervention is successful, the intervention can be maintained, decreased over time, stopped, or combinations thereof, depending on the nature of the impairment and/or the intervention. If the intervention is not successful, the cognitive impairment can be treated (e.g., through an alternative intervention) based upon the re-evaluation of the patient.

In the depicted embodiment, the steps of re-evaluating the patient and the invention are continued until the invention is determined to be successful.

Figure 2:
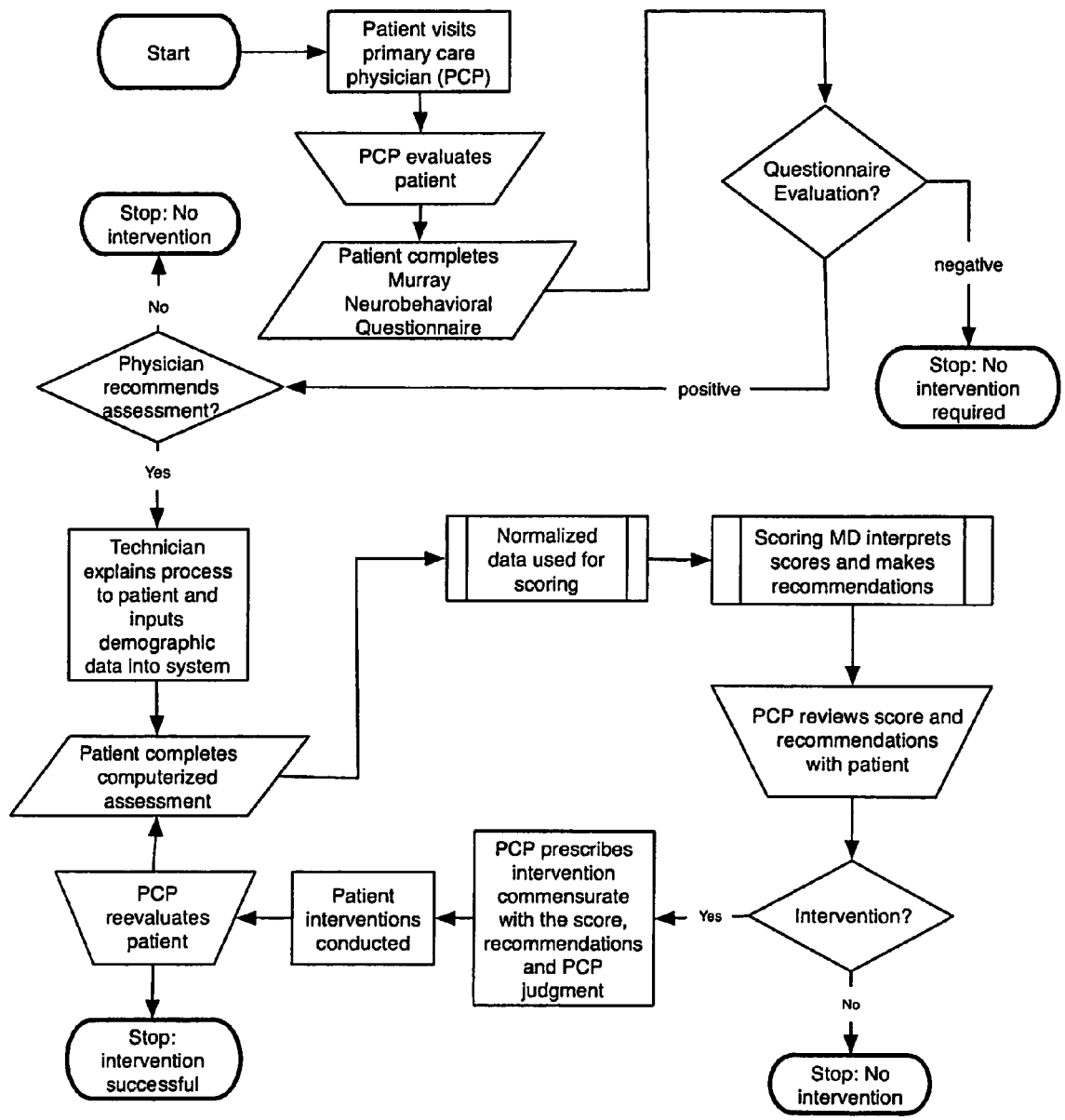
FIG. 2 illustrates a flow chart of another embodiment of an evidence-based, neuro-cognitive testing methodology and system according to the present disclosure.

FIG. 2 illustrates a flow chart of another embodiment of an evidence-based, neuro-cognitive testing methodology and system according to the present disclosure.

As shown in FIG. 2, a patient visits a primary care physician (PCP). The primary care physician evaluates the patient. The patient completes a neurobehavioral questionnaire (e.g., the Murray Neurobehavioral Questionnaire). The neurobehavioral questionnaire is evaluated to determine if intervention is needed. The protocol can be terminated if no intervention is needed, or continued if intervention is needed.

The physician can then conduct one or more additional assessments, depending on the outcome of the questionnaire (e.g., if one or more trigger questions indicates a need for an additional index, inventory, scale, and/or checklist). The protocol can be terminated if the patient accepts no assessment or if it is determined that no assessment is needed. While embodiments usable within the scope of the present disclosure are not limited to specific questionnaires, assessments or means of implementing such questionnaires or assessments, a computer system can be used to administer such materials (e.g., in conjunction with explanations by a trained technician). The demographic data of the patient can be input into the computer system, and the computerized assessment by the patient can be used to create a patient database.

Normalized data can be applied to the patient database for creating patient normalized data. The patient normalized data can be analyzed, e.g., by a physician (other than the patient's primary care physician), and one or more outcomes indicated by the patient responses to the questionnaire and/or the assessments can be determined.

Recommendations are proposed based upon the interpreted patient normalized data; The primary care physician can review the outcomes initially; and then, the primary care physician can review the outcomes and the associated recommendations with the patient for purposes of determining the need and/or applicability of an intervention. Alternatively, the primary care physician can receive the outcomes and recommendations and review with the patient for determining the need for an intervention.

The need for intervention is determined, if any. The protocol can be terminated if no intervention is needed. The protocol can be continued if a need for intervention is determined.

An intervention (e.g., treatment of the patient), commensurate with the outcome of the questionnaire and/or assessments, and with the recommendations and judgment of the primary care physician, can be prescribed and conducted.

The patient can be re-evaluated after the patient interventions are conducted. The protocol can be terminated if the intervention is successful. The protocol can be continued, if the intervention is not successful, e.g., by completing another computerized assessment of the patient, to create an updated patient database for analysis.

Work Flow—Physician's View

Figure 3:
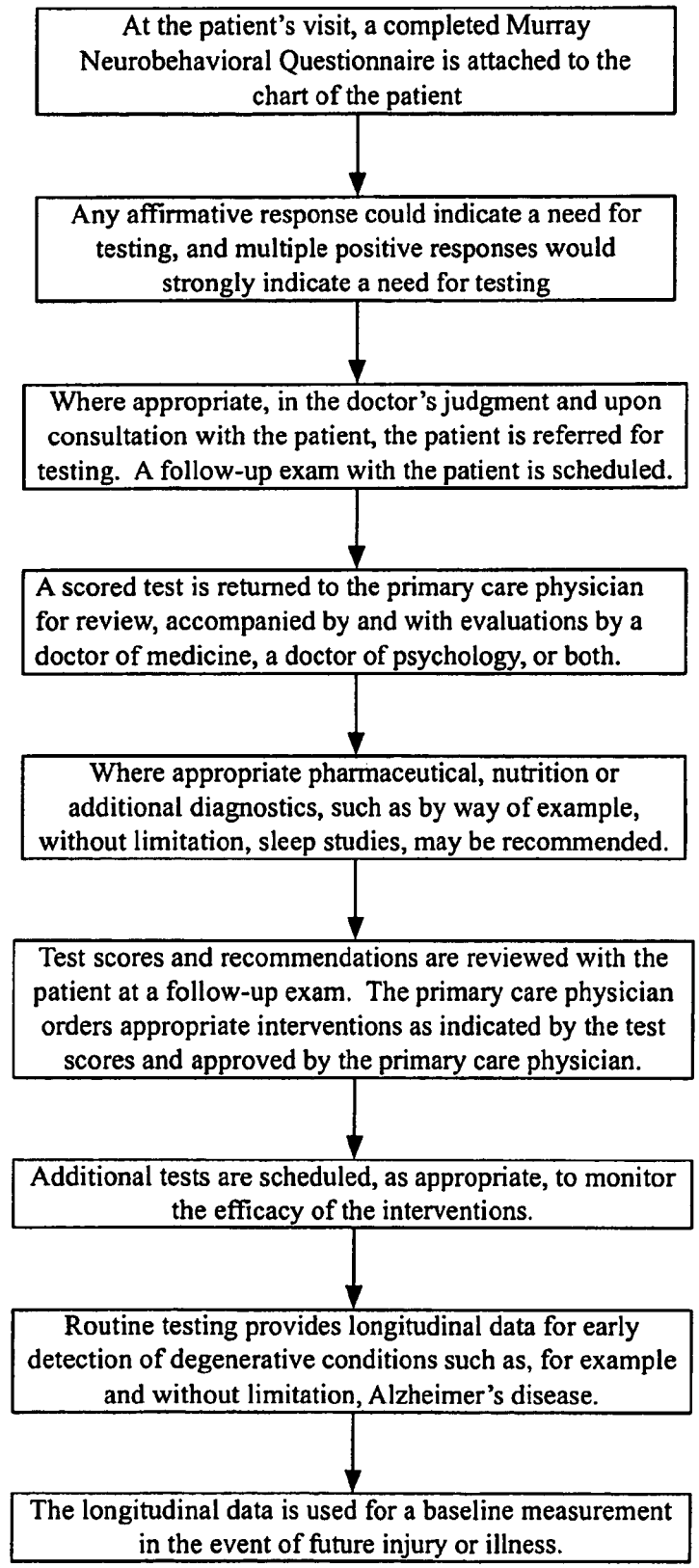
FIG. 3 illustrates a flow chart of an embodiment of workflow associated with an evidence-based, neuro-cognitive testing methodology, protocol and system according to the present disclosure.

FIG. 3 illustrates a flow chart of an embodiment of a workflow associated with the evidence-based, neuro-cognitive testing methodology, protocol and system according to the present disclosure. Specifically, FIG. 3 depicts a primary care physician's view of the methodology of the present disclosure. At the patient's visit, a completed Murray Neurobehavioral Questionnaire can be attached to the chart of the patient, e.g., the patient can complete the questionnaire via computer prior to his or her appointment with the physician, such as through a prior meeting with a technician. The completed Murray Neurobehavioral Questionnaire can thereby be available for review by the physician at the beginning of examination, and throughout. In an alternative embodiment, the physician can examine the patient and subsequently request the patient to complete a Murray Neurobehavioral Questionnaire for formulating a potential diagnosis of the patient. Any affirmative (e.g., positive) response indicated by the questionnaire could indicate a need for additional testing and/or assessment, while the totality of the patient's responses can themselves constitute an additional assessment for analysis. Where appropriate, in the physician's judgment and upon consultation with the patient, the patient can be referred for additional testing, and a follow-up examination with the patient can be scheduled.

A scored (e.g., interpreted, analyzed, and/or normalized) questionnaire, test, and/or assessment can be provided to the primary care physician for review, accompanied by and with evaluations, recommendations, and/or possible diagnoses by a doctor of medicine, a doctor of psychology, or both. Where appropriate, pharmaceutical information or diagnostics, nutritional information or diagnostics, or additional diagnostics, such as by way of example, but without limitation, sleep studies, may be recommended. Test scores and recommendations can be reviewed with the patient at a follow-up examination. The primary care physician can order appropriate interventions as indicated by the outcome of the questionnaire and/or any additional assessments.

Additional tests and/or questionnaires can be scheduled, as appropriate, to monitor the efficacy of the interventions. Each test is Medicare-approved up to four times per year. Use of the Murray Neurobehavioral Questionnaire to arrive at a potential diagnosis enables Medicare codes to be applied to each appointment. Routine testing provides longitudinal data for early detection of degenerative conditions such as, for example and without limitation, Alzheimer's disease. The longitudinal data is used for a baseline measurement in the event of future injury or illness.

Work Flow—Provider's View

Figure 4:
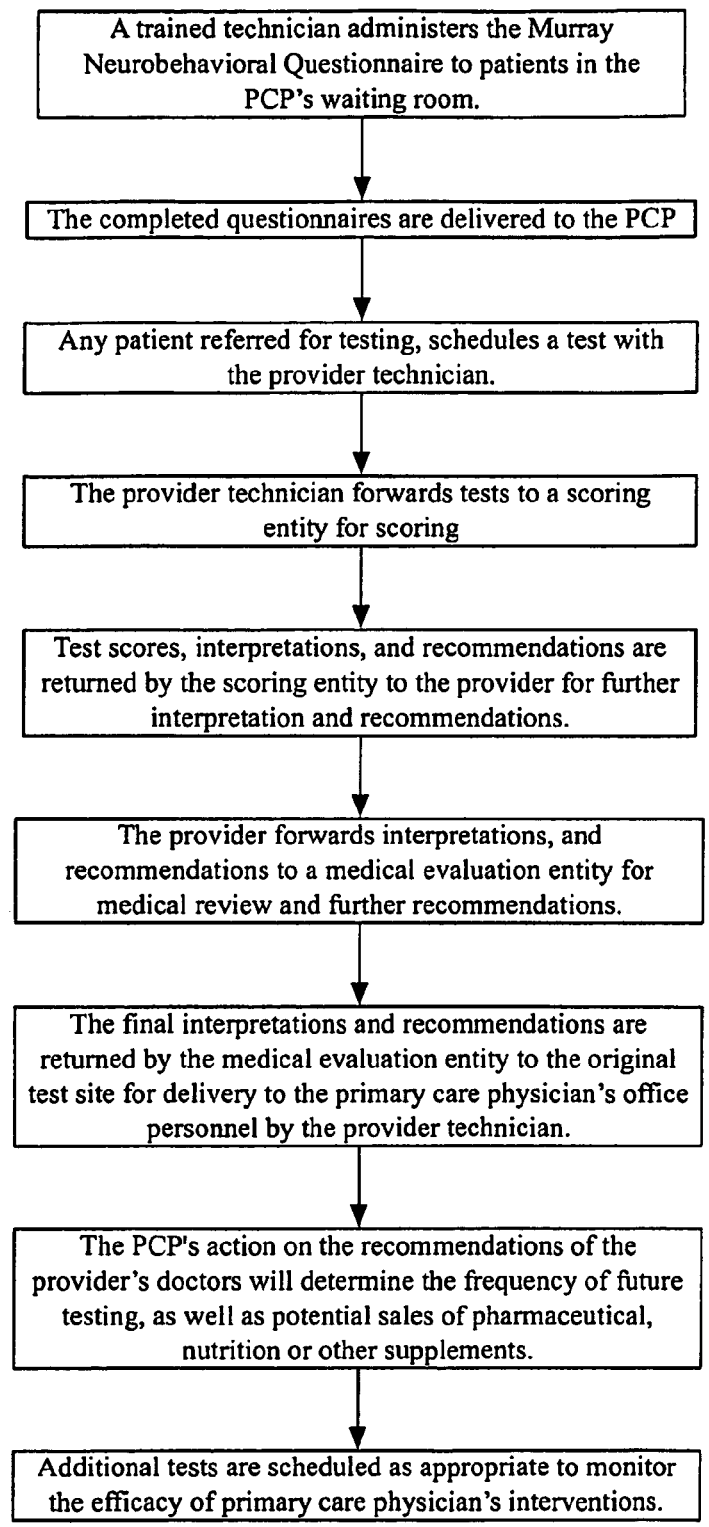
FIG. 4 illustrates a flow chart of another embodiment of workflow associated with an evidence-based, neuro-cognitive testing methodology and system according to the present disclosure.

FIG. 4 illustrates a flow chart of another embodiment of a workflow associated with the evidence-based, neuro-cognitive testing methodology and system according to the present disclosure. A medically-trained individual, including for example a medical technician, can administer the Murray Neurobehavioral Questionnaire to patients in the primary care physician's (PCP's) waiting room or another suitable location. The completed questionnaires can be delivered to personnel in the primary care physician (PCP)'s office. Alternatively, the completed questionnaires can be clipped directly to the medical chart of each patient, depending on standard operating procedures of the particular office.

Any patient, referred for additional assessments and/or testing, can schedule a test with the provider technician. Alternatively, in an embodiment, a computerized assessment can provide the patient with additional assessments, inventories, scales, and/or checklists instantaneously, after receiving a response to a question on the initial questionnaire that indicates a need for an additional assessment. Walk-in appointments can be used as an alternative to scheduled appointments; however, typically, a provider technician would administer tests by appointment. The provider technician can be responsible for maintaining the workflow and for calendaring future workflow.

The provider technician can then forward tests to a physician or other entity for analysis and/or determination of an outcome corresponding to the patient responses, such as by way of example, CNS Vital Signs. Further, the provider technician can forward the tests and billing information to a billing and collection entity, or alternatively, can directly (e.g., independently) create and transmit a bill.

Interpretations, and recommendations can be returned by the physician or other entity to the provider for further interpretation and recommendations. The provider can then forward interpretations and recommendations to a medical evaluation entity for medical review and further recommendations, such as by way of example, a Unit Medical Director (UMD). The final interpretations and recommendations can be returned by the medical evaluation entity to the original test site for delivery to the primary care physician's office by the provider technician. In an embodiment, the complete cycle of steps can be accomplished in under five days. In other embodiments, results can be returned to the primary care physician within 24-72 hours. In a further embodiment, such as when a computerized questionnaire is provided to a patient and a computer algorithm is used to analyze the patient responses, initial results can be obtained nearly instantaneously.

The primary care physician's action on the recommendations of the provider's doctors can be used to determine the frequency of future testing, as well as potential sales of pharmaceutical, nutrition or other supplements. Additional tests can be scheduled as appropriate to monitor the efficacy of the primary care physician's interventions.

The present disclosure thereby provides for a methodology for evaluating specific characteristics within a patient. The patient can visit his or her primary care physician (PCP) for evaluation with respect to an illness presently experienced by the patient.

During the office visit with the primary care physician, the patient can complete the "Murray Neurobehavioral Questionnaire," or a similar questionnaire or similar tool that includes a plurality of questions or other elements that elicit a patient response. An embodiment of the "Murray Neurobehavioral Questionnaire" can provide substantially the following questions:

1. I sometimes become easily fatigued.
2. I frequently have disrupted sleep.
3. I have headaches more than once or twice per month.
4. I feel as though my memory is not as good as it once was.
5. I have had one or more major life events in the past 18 months (death, divorce, loss of job, etc.).
6. I don't feel good about myself.
7. I feel sad often.
8. I have lost interest in things that once made me happy.
9. I think I may be depressed.
10. My family and/or friends have noticed changes in my behaviors.
11. I sometimes feel anxious for little or no reason.
12. My appetite has recently changed.
13. I have recently gained/lost weight that was not purposeful.
14. I am sleeping more than normal.
15. I am sleeping less than normal.
16. I have become aware that I am easily distracted and sometimes confused more than I used to be.
17. I sometimes have difficulty concentrating or making decisions.
18. I often feel irritable or aggressive with little or no provocation.
19. I have had a concussion in my life.
20. Alzheimer's disease on one or both sides of my family
21. My motor coordination is substantially below normal (dizziness, clumsiness, poor handwriting, etc.).
22. I experience pain that interferes with my life more than three days per week.

As such, the questionnaire includes a plurality of questions, to which the totality of the responses received from a patient can be assessed and used in the formation of one or more prospective diagnoses. Additionally, one or multiple questions can specifically function as triggers, used to provide an indication for an additional inventory. For example a positive response to question #1, above, may indicate that conducting the Epworth Sleepiness Scale may be beneficial. Positive responses to question #2 and/or question #15 may indicate that the Pittsburgh Sleep Quality Index should be performed. A positive response to question #5 may indicate that a life event checklist should be completed. Positive responses to question #6 and/or question #7 may indicate that the Self Administered Geriatric Depression Scale or Zims Self Administered Depression Scale should be administered. A positive response to question #10 may indicate that the Zugs Self Administered Anxiety Scale should be administered. A positive response to question #16 may indicate that the Neurobehavioral Symptom Inventory should be performed. A positive response to question #17 may indicate that the Alert Readiness Scale should be administered. A positive response to question #19 may indicate that the Post Concussion Symptom Scale should be administered. A positive response to question #21 may indicate that the Dizziness Health Inventory should be performed. A positive response to question #22 may indicate that the Pain Catastrophizing Scale should be administered. To facilitate use and ready evaluation/comprehension of the questionnaire results by a physician or other practitioner, the questions within the questionnaire can be categorized and/or color-coded. For example, embodied questionnaires usable within the scope of the present disclosure can include separate colors and/or sections that differentiate questions that indicate issues relating to sleep, depression, anxiety, or neurological issues (e.g., head injury).

It should be readily understood that responses to any question or combination of questions can be used as an indication for use of one or more additional analytical tools, inventories, scales, indexes, etc., and that the above description is intended as non-limiting examples of such a feature. In an embodiment, during computerized collection of responses from a patient, a response that indicates a need for an additional analytical tool can cause additional questions corresponding to the particular inventory, scale, and/or index to be contemporaneously and seamlessly added to the questionnaire.

In addition to the Murray Neurobehavioral Questionnaire and/or a similar plurality of questions, a question asking a patient to evaluate his or her functionality (e.g., emotional, social, and/or occupational functionality) can be provided. For example, a subjective assessment, such as a listing of categories from the General Assessment of Functioning (GAF) scale, can be provided, accompanied by a description of each category, enabling a patient to select the category that he or she believes to be applicable. A scoring physician can use the patient's responses to the questionnaire and/or other factors in making an independent assessment of the patients' functionality, creating a unique plurality of measurements, in which the patient's self-assessment, the physician's independent assessment, and any differential between the two assessments can all be used in formulating a potential diagnosis and/or course of treatment. For example, a geriatric patient, who is concerned with regard to a loss of independence, may exaggerate his or her functionality, while a depressed patient may provide an abnormally low self-assessment, absent any factors that would cause a physician to provide a low assessment, such that the results in both cases could provide a differential that would facilitate the analysis and formation of a potential diagnosis of each patient.

By way of example, an embodiment of a functionality question can include the following categories and descriptors:

| | |
|---|---|
| 91-100 | Superior - no problems |
| 81-90 | Good - minimal problems |
| 71-80 | Slight - only expected life problems |
| 61-70 | Mild problems - some difficulties |
| 51-60 | Moderate - difficulties with work, family, school (few friends, |

|       | frequent conflicts)                                                                                              |
|-------|------------------------------------------------------------------------------------------------------------------|
| 41-50 | Serious problems - (no friends, can't keep a job)                                                                |
| 31-40 | Major impairments - (abuse, neglect of self and others)                                                          |
| 21-30 | Inability to function in almost all areas (sometimes consider suicide, stay in bed all day, no job, no friends, very unhappy) |
| 11-20 | Some danger - (to self or others)                                                                                |
| 01-10 | Persistent danger - (to self or others; recurrent violence, unable to maintain hygiene or serious attempts of suicide) |

In administering the above question and/or a similar question regarding a patient's functionality, a patient can be requested to indicate which category would apply at the particular time the question is answered, and which category applies on most days during the preceding month. These two responses can be weighted differently (e.g., 1:2). It is noted that normally, the GAF scale and/or similar subjective analyses of patient functionality are exclusively scored by physicians, and that use of a patient self-assessment both alone and alongside a physician assessment to determine any differential, can provide valuable information, especially when used in conjunction with the Murray Neurobehavioral Questionnaire and/or similar questionnaires, inventories, scales, indices, checklists, etc.

When the Murray Neurobehavioral Questionnaire is evaluated, if the evaluation is negative (e.g., no responses to trigger questions indicate a need for additional assessments, and the totality of the patient's responses to the questions do not themselves indicate a need for intervention), then no intervention is required. However, if the evaluation of the Murray questionnaire is positive, then the physician can recommend one or more additional assessments. If the assessments are determined to be negative, and the questionnaire, itself, does not indicate a need for intervention, then no intervention is required. However, if the assessment is positive, a medically-trained individual can acquire further input from the patient, explain the process to the patient, input demographic data into the system, and have the patient complete the computerized assessment.

Standard, normalized data can be used for evaluating the computerized assessment. A physician can interpret the patient responses and make recommendations based upon the outcome indicated by interpretation of the responses.

The outcome and associated recommendations can be forwarded to the primary care physician for review and provision of recommendations to the patient. The patient, in conjunction with the primary care physician, can determine whether an intervention is required. If the determination is that no intervention (e.g., treatment of the patient) is required, the process will be terminated. However, if it is determined that an intervention is appropriate, further action can be taken.

Specifically, the primary care physician can prescribe an intervention commensurate with the outcome and the recommendations and the judgment of the primary care physician (PCP). Alternatively, the outcome assessment and the associated recommendations, by the consulting physician (e.g., the TestSmartRX physician, the Unit Medical Director), can be used to formulate a judgment by the consulting physician. Then, the judgment, which is commensurate with the outcome assessment and associated recommendations, can be given to the primary care physician (PCP).

Interventions can be actions such as, by way of example and without limitation, addressing, treating, minimizing, eliminating and/or preventing such maladies and/or illnesses as, for example, depression, sleep disorders, anxiety, anxiety and depression, or combinations thereof.

After the patient interventions are conducted, the examining or primary care physician can reevaluate the patient at set intervals. If the interventions were successful, then the protocol can be terminated. However if reevaluation indicates that the interventions should be continued, or modified, the protocol would continue.

In continuing the process, the patient can complete one or more additional computerized assessments (e.g., a questionnaire, with additional assessment tools administered as indicated by responses to the questionnaire, in combination with a functionality question/assessment). Based upon each additional computerized assessment, the data can be re-evaluated (e.g., using standard, normalized data). The interpreting physician can again interpret the responses and results and make recommendations to the primary care physician, for review and recommendations to the patient. Once again if it is determined that an intervention is required, then additional procedures can be undertaken. If it is determined by the patient and the primary care physician that no intervention is required, then the protocol can be terminated. Otherwise the primary care physician can prescribe additional interventions, commensurate with the outcomes of the assessments and the recommendations and the judgment of the primary care physician. From time to time the patient can again visit the examining physician for re-evaluation. During the re-evaluation with the examining and/or primary care physician, the patient can complete additional computerized assessments. This protocol can continue until such time as the patient has been successfully treated by the interventions.

Figure 5:
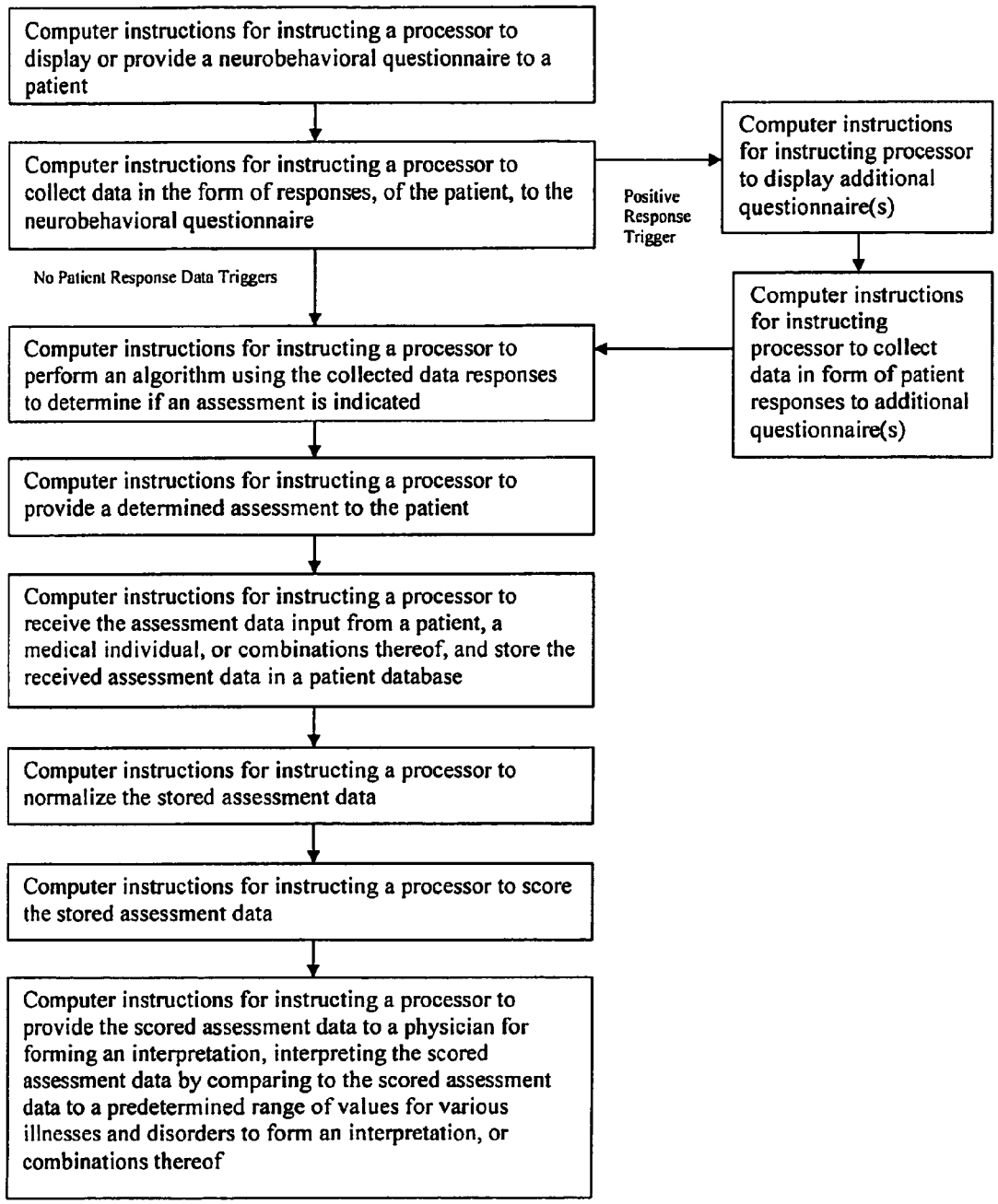
FIG. 5 illustrates a flow chart of an embodiment of an evidence-based, neuro-cognitive testing methodology, protocol and system for forming and interpreting data, according to the present disclosure.

An embodiment of the present invention is shown in FIG. 5, which includes computer instructions, provided by a computer readable medium, for instructing a processor to display a Murray Neurobehavioral Questionnaire to a patient and to collect data in the form of responses of the patient to the Murray Neurobehavioral Questionnaire. The providing or displaying of the Murray Neurobehavioral Questionnaire to the patient can be via a processor located within a computerized or technological device. Such devises can include for example, a computer coupled to a monitor for display, a digital computer, a personal digital assistant (PDA), a handheld computer, a laptop, a telephone, a computerized tablet or pad, other computerized devices, or combinations thereof.

The patient can input response data, to the Murray Neurobehavioral Questionnaire, directly into the computerized or technological device, e.g., via a keyboard, a voice activated feature, a digital recording feature, a mouse, and/or other input features for receiving the patient response data input. Alternatively, a medically-trained individual and/or technician can input the patient response data into the computerized or technological device for the patient. The medically-trained individual can include, for example, a physician, a medical technologist, a medical professional, a physician assistant, a medical technician, a medical-staff individual, an emergency medical technician, a medical secretary, a medical clerk, or other medically-trained individual. Further, the patient response data can be input into the computerized or technological devices by a combination of the patient, the medically-trained individual, and in some instances, by automation.

The patient's response data can trigger, automatically, the need for additional questions, including one or multiple additional questions that can be used to gather additional patient response data for rendering a potential diagnosis. In an embodiment, the present invention can include computer instructions for instructing a processor to automatically present additional questions to the patient, based upon the patient's response to one or more specific question(s) of the Murray Neurobehavioral Questionnaire, for gathering additional patient response data inventory. For example, a positive response to question #1 of the Murray Neurobehavioral Questionnaire may indicate that conducting the Epworth Sleepiness Scale may be beneficial for rendering a potential diagnosis of the patient with regard to a possible sleep disorder, whereas a positive response to question #19 of the Murray Neurobehavioral Questionnaire may indicate that a Post Concussion Symptom Scale should be administered to assist in determining a potential diagnosis and treatment relating to a prior head injury. The embodied questionnaires (i.e., additional questions), that are usable within the scope of the present disclosure, can include separate colors and/or sections or categories that can differentiate the questions, which can indicate the issues relating to sleep, depression, anxiety, or neurological issues (e.g., head injury). Further, the embodiment of the present disclosure can include computer instructions for instructing the processor to collect the patient response data from the additional questions to supplement the existing patient response data inventory or form an additional patient response data inventory.

The computerized or technological device for displaying, receiving, storing and analyzing data can include an integrated processor, or a processor can communicate with the device via a wireless connection, a wired connection, or combinations thereof. After receiving and collecting the patient response data, the processor can perform an algorithm, using the collected responses of the patient, to determine if any additional assessments are indicated. In an embodiment, an indication for additional assessments and administration of the additional assessments can be performed automatically and contemporaneously. For example, if a patient selects a response to a question provided in the initial Murray Neurobehavioral Questionnaire that indicates a need for an additional assessment, questions corresponding to the additional assessment can be seamlessly added to the questionnaire, e.g., at the end thereof. As the processor collects the patient response data, the processor can communicate with memory, which can be encompassed within, or alternatively in remote or direct communication with, the computerized or technological device, for storing the patient's response data. The memory can include various devices for storing the collected patient response data, including a hard disk, a flash memory, an optical digital storage device, and other memory and storage devices for storing the patient response data in the forms of digital data, analog data, or combinations thereof. The memory can include computer instructions, adapted to be executed by the processor, which use the collected patient response data to perform the algorithms for determining if additional assessments of the patient are needed, and/or to provide a potential diagnosis based on patient responses to the questionnaires and/or additional assessments.

As shown in the embodiment in FIG. 5, an assessment is determined to be necessary and computer instructions are provided by the computer readable medium for instructing the processor to provide an assessment or test to the patient, to receive assessment data input of the patient, and to store the received assessment data in a patient database. The assessment data input can be provided by the patient, a medical individual, or combinations thereof. In some instances the assessment data input can be provided to the processor by computerized automation. The patient databases can include the memory or a separate database storage for patient data, wherein the database storage is in communication with the processor. For example, a processor, that is stored within a computerized device, can be coupled to a server via a network, which can include the Internet, a LAN (local area network), a WAN (wide area network), an intranet, a communications network, a computer network, or combinations thereof. The server can be coupled to the patient database storage for enabling communication between the processor and the patient database storage.

The database storage typically stores data on a magnetic medium, such as a magnetic disk; however, other storage media, known in the art, can also be used. The database storage device can store, for example, the patient response data, the patient assessment data, and other patient data files and documents for assessing the patient's condition and interpreting the patient's data for obtaining potential diagnoses and/or appropriate interventions for the patient. The patient's data documents can be in the form of word processing documents, spreadsheet documents, graphics, HTML (Hypertext Markup Language) documents, and other forms of such documents, and the data can be digital, analog, or combinations thereof.

The computer readable medium for providing the computer instructions to the processor for performing the methodologies and protocols can include, for example, a Compact Disk Read Only Memory (CD-ROM), a floppy disk, a Zip™ Disk, or another computer readable medium as known in the art for storing computer instructions and distributing the instructions as software. The computer readable medium can be provided within the computerized or technological device for instructing the processor, or can be provided to the patient or medically-trained individual with the computerized or technological device for instructing the processor to perform the methodologies and protocols.

The embodiment, shown in FIG. 5, further includes computer instructions for instructing the processor to normalize the stored assessment data, score the stored assessment data (e.g., determine outcomes and/or results indicated by patient responses), and provide the scored assessment data to a physician for forming an interpretation. Alternatively, the processor can be instructed to interpret the assessment data by comparing to the assessment data to a predetermined range of values, responses, and/or prospective outcomes indicative of various illnesses and disorders to form an interpretation (e.g., a potential diagnosis). Further, the interpretation can be formed by a combination of the comparisons and analyses conducted by the processor and the review and analysis by the physician of the scored assessment data. Further, the processor can be in communication with the memory and/or the patient databases for performing one or more of the steps of normalizing the stored assessment data, scoring the stored assessment data, providing the scored assessment data to the physician, and comparing and analyzing the scored assessment data for forming an interpretation.

Figure 6:
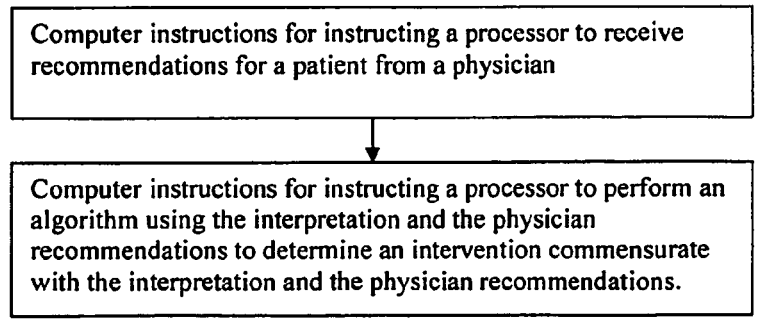
FIG. 6 illustrates a flow chart of another embodiment of an evidence-based, neuro-cognitive testing methodology and system for analyzing data and determining interventions, according to the present disclosure.

FIG. 6 depicts another embodiment, in which a computer readable medium can include computer instructions for instructing a processor to receive recommendations for a patient from a physician, and to perform an algorithm using the interpretation and the physician recommendations to determine an intervention commensurate with the interpretation and the physician recommendations.

Figure 7:
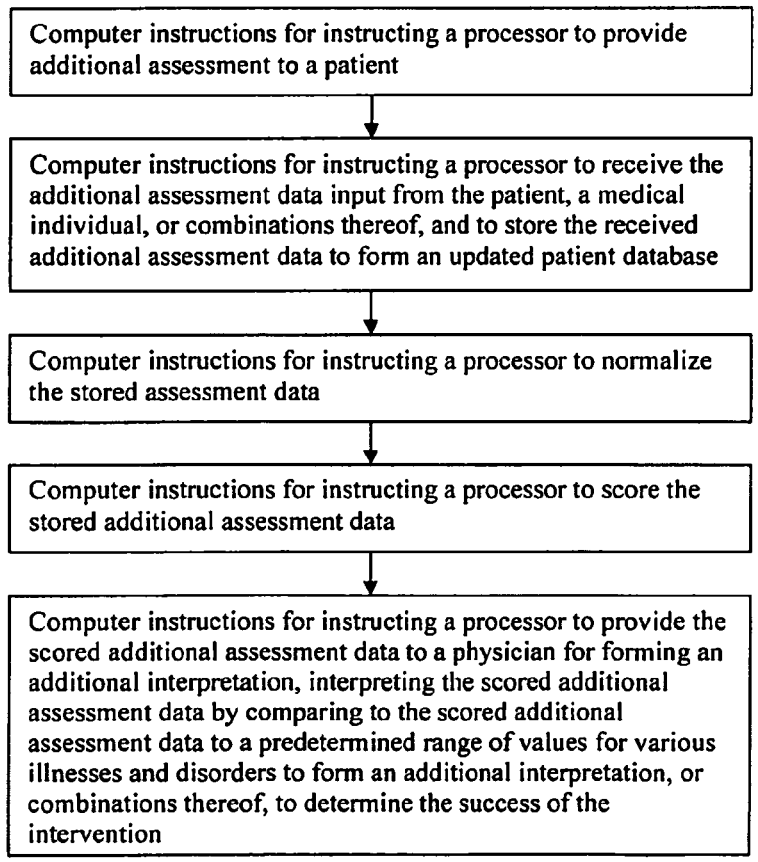
FIG. 7 illustrates a flow chart of an embodiment an evidence-based, neuro-cognitive testing methodology, protocol and system for receiving and analyzing additional assessments and for forming and using interventions, according to the present disclosure.

In FIG. 7, an embodiment of the present invention is shown in which a computer readable medium includes computer instructions for instructing a processor to provide an additional assessment to a patient, receive additional assessment data from the patient, and store the additional assessment data to form an updated patient database. The embodiment shown in FIG. 7 further includes computer instructions for instructing the processor to normalize the additional assessment data, score the additional assessment data (e.g., determine outcomes indicated by patient responses), and provide the scored additional assessment data to a physician for forming an additional interpretation, e.g., to determine the success of an intervention. Alternatively, the processor can receive the computer instructions to interpret the scored additional assessment data by comparing the scored additional assessment data to a predetermined range of values for various illnesses and disorders to form an additional interpretation, which is then usable to determine the success of the intervention. Further, the additional interpretation can be formed by a combination of the comparisons and analysis conducted by the processor and the review and analysis by the physician of the scored additional assessment data, for determining the success of the intervention.

Figure 8:
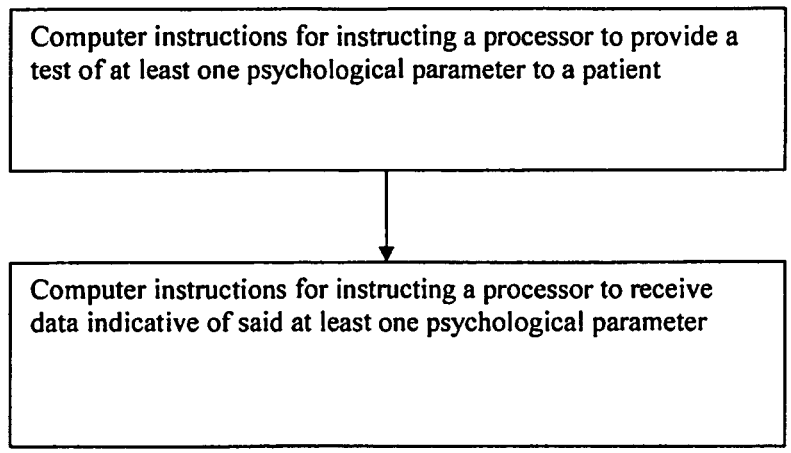
FIG. 8 illustrates a flow chart of another embodiment of an evidence-based, neuro-cognitive testing methodology and system for analyzing data and forming possible diagnosis and additional assessments, according to the present disclosure.

FIG. 8 depicts an embodiment of the present invention that includes computer instructions for instructing a processor to provide a test of at least one psychological parameter to a patient, and to receive data indicative of said at least one psychological parameter. For example, a computerized device comprising a processor can be used to provide a test (e.g., a questionnaire) to the patient in regard to whether the patient presents with symptoms of anxiousness, fatigue, and/or unexplained sadness or depression. Then, based upon the patient's response data, as input into the computerized device or as automatically detected and recorded by the computerized device, a determination can be made as to whether the patient response data is indicative of a possible diagnosis of anxiety and/or depression. Patient responses to specific questions can be used to form an indication of an additional assessment that may be beneficial. In an embodiment, the computerized device can automatically administer the additional assessment when such an indication is determined.

Figure 9:
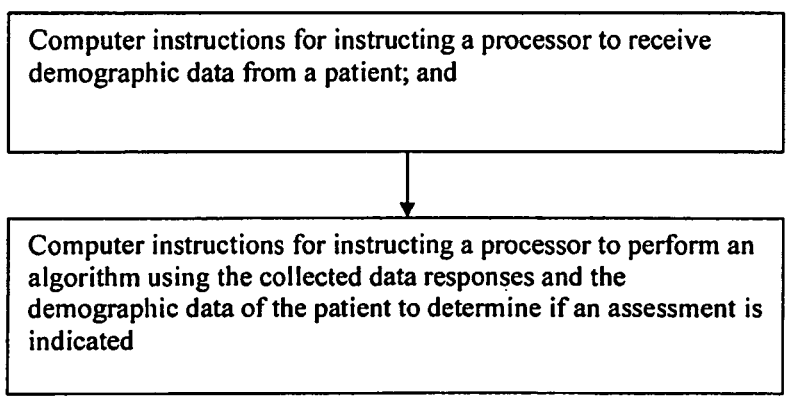
FIG. 9 illustrates a flow chart of another embodiment of an evidence based, neuro cognitive testing methodology and system according to the present disclosure.

FIG. 9 depicts another embodiment, in which computer instructions are provided for instructing a processor to receive demographic data from a patient, and to perform an algorithm using the collected data responses and the demographic data to determine if an assessment is indicated. For example, a computerized device comprising a processor can be used for receiving the age of a patient, as input into the computer device by the patient or a medically-trained individual. The processor, in communication with a memory or patient database storage, can process and store the age demographic patient information. At a later time, the processor can recall the age demographic patient information and combine the demographic information with the patient response data, which the processor received and collected from the patient in response to the Murray Neurobehavioral Questionnaire. Then, the processor can perform an algorithm using the combined age demographic patient information and the patient response data to determine if an assessment is needed. For example, with age, other conditions such as stroke, brain tumors, dementia, some vitamin deficiencies, and some chronic diseases can cause cognitive impairment. However, if this underlying cause is properly assessed, interpreted, and treated (e.g., intervention to treat the brain tumor, vitamin deficiency, or chronic disease), then the cognitive impairment can be reversible.

For each embodiment applicable with respect to the present disclosure, follow-up areas are available. Examples of such follow-up areas are: Senile dementia uncomplicated; Pre-senile dementia uncomplicated; Pre-senile dementia with depressive features; Other persistent mental disorders due to conditions classified elsewhere; Unspecified persistent mental disorders due to conditions classified elsewhere; Unspecified episodic mood disorder; Anxiety state unspecified; Generalized anxiety disorder; Other pain disorder related to psychological factors; Unspecified acute reaction to stress; Post Traumatic Stress Disorder; Unspecified adjustment reaction; Personality change due to conditions classified elsewhere; Post Concussion Syndrome; Other specified non psychotic mental disorders following organic brain damage; Depressive disorder not elsewhere classified; Mixed disturbance of conduct and emotions; Unspecified disturbance of conduct; Oppositional defiant disorder; Academic underachievement disorder of childhood or adolescence; Attention deficit disorder of childhood without hyperactivity; Attention deficit disorder of childhood with hyperactivity; Mild intellectual disabilities; Unspecified intellectual disabilities; Alzheimer's disease; Senile degeneration of brain; Altered Mental Status; Neurological Neglect Syndrome; Late effect of fracture of skull or face bones; Unspecified adverse effect of unspecified drug, medicinal, biological substance; Late effect of intracranial injury without mention of skull fracture; Head injury, unspecified; Unspecified child abuse; Other child abuse and neglect; Unspecified adult maltreatment; Other adult abuse and neglect; Human immunodeficiency virus disease; Unspecified mental disorder & developmental handicap (screening); Other neurological conditions (screening).

While certain exemplary embodiments have been described in details and shown in the accompanying drawings, it is to be understood that such embodiments are merely illustrative of and not devised without departing from the basic scope thereof, which is determined by the claims that follow.

What is claimed is:

1. A method for evaluating a patient utilizing a questionnaire, the method comprising the steps of:
   providing to the patient a questionnaire comprising a plurality of questions, the questionnaire eliciting from the patient only affirmative or negative responses to the plurality of questions wherein at least one of said questions corresponds to at least one additional inventory;
   providing to the patient a functionality question relating to subjective assessment of functionality of the patient;
   receiving a response from the patient to each of the plurality of questions and to the functionality question;
   inputting responses to the plurality of questions and to the functionality question received from the patient into a computer system to create a patient database;
   analyzing the response to each of the plurality of questions, the response to the functionality question, or combinations thereof, to determine an indication of additional inventories;
   providing to the patient additional inventories corresponding to the indication comprising automatically adding at least one additional question to the questionnaire concurrent with a determination of the indication for an additional inventory, receiving responses from the patient thereto, and analyzing the responses to the additional inventories;
   assessing the patient by a first physician and recording a functionality assessment corresponding to the patient, wherein the functionality assessment and a patient's response to the functionality question define a differential;
   using the response to each of the plurality of questions, the response to the functionality question, the responses to the additional inventories, the functionality assessment, the differential, or combinations thereof, to form a first patient assessment comprising at least one potential diagnosis of the patient; and
   communicating said at least one potential diagnosis of the patient to a second physician.

2. The method of claim 1, wherein the steps of providing to the patient the questionnaire, the functionality question, and the additional inventories, and wherein the steps of receiving responses from the patient comprise using a processor in communication with an input device and a display device to display the questionnaire, the functionality question, and the additional inventories to the patient and to receive inputs corresponding to the responses from the patient.

3. The method of claim 1, wherein the step of providing to the patient the functionality question comprises providing to the patient a plurality of numeric ranges corresponding to a Global Assessment of Functioning (GAF) scale and associated descriptors for each range and receiving a selection of a numeric range from the patient.

4. The method of claim 1, wherein the step of assessing the patient by the first physician and recording the functionality assessment comprises using the response to each of the plurality of questions, the response to the functionality question, the responses to the additional inventories, or combinations thereof, to formulate the functionality assessment.

5. The method of claim 1, further comprising the steps of:
providing to the patient a follow-up questionnaire, a follow-up functionality question, or combinations thereof, after treatment responsive to said at least one potential diagnosis has been administered;
receiving responses from the patient to the follow-up questionnaire, the follow-up functionality question, or combinations thereof; and
assessing the responses to the follow-up questionnaire, the follow-up functionality question, or combinations thereof, to form a second patient assessment and comparing the responses to the first patient assessment to determine efficacy of the treatment.

* * * * *